(12) United States Patent
Kuhn

(10) Patent No.: US 6,896,233 B2
(45) Date of Patent: May 24, 2005

(54) SUPPORT FOR MEDICAL EQUIPMENT

(75) Inventor: Peter Kuhn, Munich (DE)

(73) Assignee: Mavig GmbH, Munich (DE)

( * ) Notice: Subject to any disclaimer, the term of this patent is extended or adjusted under 35 U.S.C. 154(b) by 89 days.

(21) Appl. No.: 10/344,204

(22) PCT Filed: Jul. 6, 2001

(86) PCT No.: PCT/EP01/07783
§ 371 (c)(1),
(2), (4) Date: Feb. 10, 2003

(87) PCT Pub. No.: WO02/14734
PCT Pub. Date: Feb. 21, 2002

(65) Prior Publication Data
US 2003/0183737 A1 Oct. 2, 2003

(30) Foreign Application Priority Data

Aug. 17, 2000 (DE) .......................................... 100 40 338
Sep. 6, 2000 (DE) .......................................... 100 43 895

(51) Int. Cl.$^7$ ................................................. A47H 1/10
(52) U.S. Cl. .................. 248/323; 248/284.1; 248/291.1
(58) Field of Search ................................. 240/323, 324, 240/325, 285.1, 279.1, 280.11, 298.1, 299.1

(56) References Cited

U.S. PATENT DOCUMENTS 3,574,340 A * 4/1971 Busche ..................... 248/285.1
5,127,617 A * 7/1992 Bergetz .................... 248/278.1
5,139,223 A * 8/1992 Sedighzadeh ................ 248/324
5,609,316 A * 3/1997 Tigliev ................... 248/123.11
6,199,812 B1 * 3/2001 Schuepbach ................ 248/324

FOREIGN PATENT DOCUMENTS

| CH | 648 466 A5 | 3/1985 |
| DE | 41 20 260 C1 | 1/1993 |
| DE | 297 06 015 U1 | 5/1997 |
| DE | 200 15 398 U1 | 1/2001 |
| EP | 0 516 475 A1 | 12/1992 |
| WO | WO 98/52484 | 11/1998 |

\* cited by examiner

Primary Examiner—Leslie A. Braun
Assistant Examiner—Tan Le
(74) Attorney, Agent, or Firm—Scully, Scott, Murphy & Presser

(57) ABSTRACT

A support (1) for bearing at least one piece of equipment (2,3,4), in particular video display units and other medical equipment. The support includes a support arm (5), to which the equipment (2,3,4) can be at least indirectly fixed and a fixing device (6), which engages in a connecting section (7) of the support arm (5) for suspending the support (1). The point of engagement (12) can be changed, to displace the center of gravity (16) of the support arm (5) and its load for a predetermined angle of the support arm (5), so that it lies at least approximately below the suspension point, at which the support (1) is suspended by the fixing device (6).

11 Claims, 3 Drawing Sheets

SUPPORT FOR MEDICAL EQUIPMENT

The invention concerns a support for medical equipment, particularly visual display units (VDUs), in the context of medical applications.

To support medical equipment, in hospitals, medical practices and similar facilities, supports which are suspended from the ceiling of the treatment room or operating theatre via a sprung arm are used. This ensures that the floor of the treatment room or operating theatre is always freely accessible and in particular easy to clean and disinfect, so that the hygienic requirements can be fulfilled. The known support consists of a C-shaped support arm and a transverse support which is fixed to it. The known support is designed for a particular equipment structure. The support, which is designed for a structure consisting of three VDUs, is described in more detail below. The VDUs have a defined size and weight distribution. The geometrical ratios and weight distributions of the support are defined on this basis, so that the support, which is suspended on a fixed suspension point on the sprung arm, supports the VDUs, which are fixed to the support, without the support arm being significantly inclined or significant torque forces acting on the suspension point.

The known support has several disadvantages. Since the support is designed on the basis of the weight distribution and the size of the specified VDUs, use of the support for other VDUs or even other medical equipment is impossible. Additionally, if the construction of the VDUs on which it is based is changed significantly, e.g. because of a product improvement or product change, this raises the problem that it is necessary to adapt the design of the support, which is expensive, reduces the production numbers of a given support type and has considerable practical disadvantages. Additionally, the known support is completely unsuitable if the medical equipment to be supported is not specified in advance, and in particular if several different pieces of medical equipment are fixed to the support alternately, depending on what is used.

The invention is therefore based on the object of creating a support which is suitable for different equipment and a different number of pieces of equipment, and which is such that a piece of equipment can be replaced and, in particular, the inclination and/or the torque which acts on the support can be adjusted.

The object is achieved by an article with the features of claim 1.

The support according to the invention has the advantage that the engagement point at which the fixing device to suspend the support engages with a connecting section of the support arm can be changed. In this way, the centre of gravity of the loaded support arm can, for an inclination which is given, for instance, by a horizontal orientation of the piece of equipment, be moved at least approximately below the suspension point, by changing the engagement point. In this way, a torque acting on the support can be prevented, and the inclination of the support arm can be adjusted if required.

Advantageous extensions of the article which is given by the features of claim 1 are possible by the measures which are listed in the subclaims.

It is advantageous that the support arm is bow-shaped, particularly C-bow-shaped. In this way the support arm can be taken round the equipment, so that the space which is provided for the equipment can be optimally used. Additionally, in this way the connecting section of the support arm is simply given by the upper, at least partially horizontally running bow of the C bow of the support arm.

It is advantageous that the fixing device has a joint, particularly a ball-and-socket joint, for suspension of the support with no torque in relation to at least one axis. For the case that the support is unevenly loaded in relation to the suspension which is determined by the choice of engagement point, because of the mobility resulting from the joint an inclination of the support arm differing from the specified inclination is set. By changing the engagement point at which the fixing device engages with the connecting section of the support arm, the inclination of the support arm can be adjusted to the specified inclination. In this way the desired inclination can be set, torque-free suspension of the support being always given.

Advantageously, at least the connecting section of the support arm has a hollow profile, so that at least in the area of the connecting section an inner space is formed. The connecting section has at least two recesses which are opposite each other, and through which the fixing device engages with the inner space of the connecting section of the support arm. In this way, a significant part of the fixing device, which is provided to change the engagement point at which the fixing device engages with the connecting section of the support arm, can be arranged in the inner space of the connecting section of the support arm, resulting in a compact construction.

Advantageously, a locking device for the fixing device, to lock the fixing device in relation to the support arm, is arranged in the inner space of the connecting section of the support arm. In this way, after a successful adjustment of the fixing device in relation to the support arm of the support, the fixing device can be locked in relation to the support arm, the locking device being housed in the support arm of the support in an inconspicuous and space-saving manner.

It is advantageous that the locking device has at least one locking plate, to which a locking force can be applied to lock the side of the inner space of the connecting section against one wall of the connecting section. It is particularly advantageous that another locking plate, which is at least substantially opposite to the locking plate in relation to the wall of the connecting section, is assigned to the locking plate, it being possible to apply the locking force to both locking plates against each other, to lock the fixing device in relation to the support arm. In this way the locking force acts on the participating components over a large area, so that because of the low contact pressure, i.e. because of the large area over which the force is distributed, the locking can be easily undone even after locking over a relatively long period. Additionally, the locking plates can be used as an integral part of the locking device, i.e. as connecting elements between components of the locking device.

Advantageously, the locking device has a locking bolt, which engages with a thread of the locking plate and is supported at least indirectly on the further locking plate when it is tightened. In this way, the same force is applied in each case to the wall (which is in contact with the locking plates on both sides) of the connecting section of the support arm, so that deformation of the wall of the connecting section, in particular in the area of the opposing recesses, is prevented.

It is advantageous that the engagement point at which the fixing device engages with the connecting section of the support arm is continuously changeable. For this purpose, it is particularly advantageous that the engagement point is changed by means of a spindle, which is carried in the support arm and can be moved along the fixing device. In this way, continuously variable, precise adjustment of the engagement point can be achieved, to move the centre of gravity of the loaded support arm, for a given inclination of the support arm, at least approximately below the suspension point. The spindle ensures advantageous force transmission, which also makes specially simple positioning of the engagement point possible.

It is also advantageous that supplementary weights can be attached to the support arm, to move the centre of gravity of the loaded support arm, for a given inclination of the support arm, with fine adjustment below the suspension point. In this way, small adjustments can easily be made. For instance, if it is a requirement that one of the pieces of equipment should be replaced relatively frequently, giving a different weight distribution, this can be compensated for using the supplementary weights, without a change of the engagement point at which the fixing device engages with the connecting section of the support arm being required.

A preferred embodiment of the invention is shown in simplified form in the drawing and described in more detail below.

Figure 1:
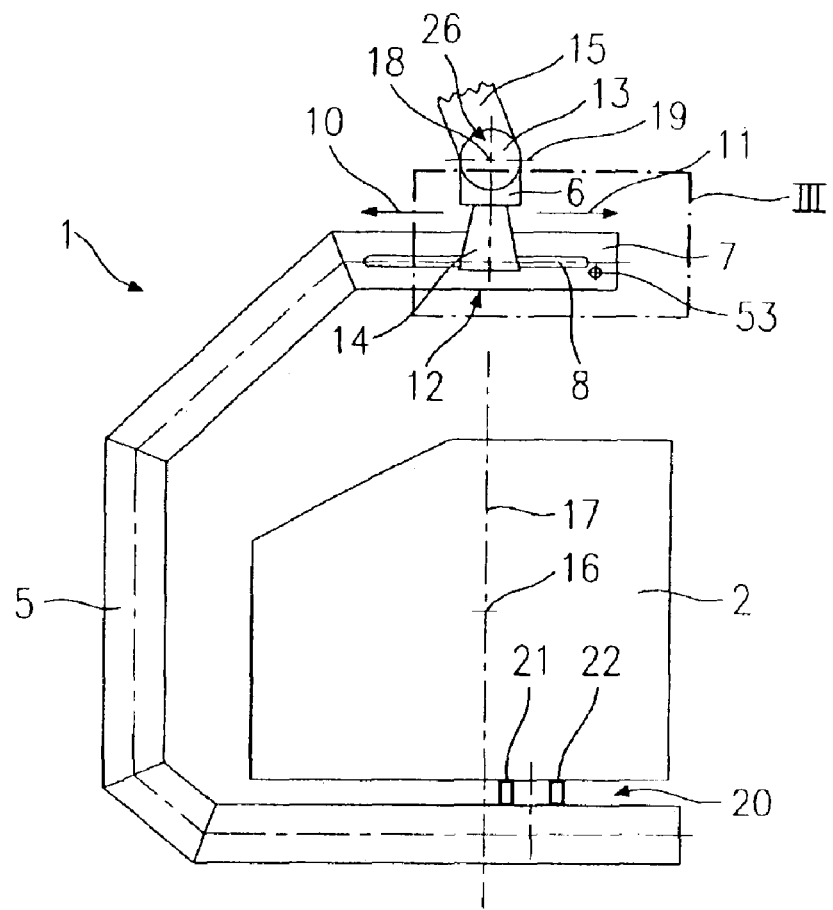
FIG. 1 shows a side view of the support according to a preferred embodiment.

FIG. 1 shows a preferred embodiment of the support 1 according to the invention, to support at least one piece of equipment 2. The support 1 is used in particular to support VDUs and other medical equipment. The preferred area of use of the support 1 is the medical area. This means that the support 1 is preferably used in clinic rooms, medical practices and similar. However, the support 1 according to the invention is also suitable for other application cases.

The support 1 has a support arm 5 and a fixing device 6. The support arm 5 is C-bow-shaped, a connecting section 7, with which the fixing device 6 engages, being provided in the upper area of the support arm 5. The engagement takes place through two opposing recesses 8, 9, of which the recess 8 is shown in FIG. 1. The fixing device 6 can be moved along the recesses 8, 9 in the directions 10, 11 in relation to the connecting section 7 of the support arm 5, so that the engagement point 12 at which the fixing device 6 engages with the connecting section 7 of the support arm 5 through the recesses 8, 9 can be changed in relation to the recesses 8, 9.

The fixing device 6 has a ball-and-socket joint 13, in relation to which a first section 14 of the fixing device 6 can be rotated in relation to the second section 15 of the fixing device 6. The second section 15 can, for instance, be fixed to a sprung arm which is fixed to the ceiling of a room. An inclination of the sprung arm in relation to the horizontal is compensated for by the ball-and-socket joint 13. Instead of the ball-and-socket joint 13, a simple joint, which can only be rotated in relation to one axis, can be used. Other joints and a combination of several joints can also be used instead of the ball-and-socket joint 13.

Because of the ball-and-socket joint 13, the support arm 5, which is loaded with the equipment 2, 3, 4, is suspended without torque, so that the centre of gravity 16 of the components which are suspended on the fixing device 6, and which include components 2 to 5, comes to lie on the vertical axis which is defined by the mid-point of the ball-and-socket joint 13. As axes of rotation, for instance the axes 18, 19, the intersection of which is at the suspension point 26, can be given.

The support arm 5 is connected to a transverse support 20, which includes the two braces 21, 22, each of which has a rectangular profile. The equipment 2, 3, 4 is fixed to the transverse support 20 of the support 1 using a conventional fixing. They can be fixed, for instance, by screwing the equipment 2, 3, 4 to the support arm 5.

In FIG. 1, additionally, a bearing pin 53, which is arranged on the connecting section 7 of the support arm 5, is shown. This bearing pin is part of a spindle bearing for a spindle mechanism, which is described in more detail below with reference to FIGS. 3 and 4.

Figure 2:
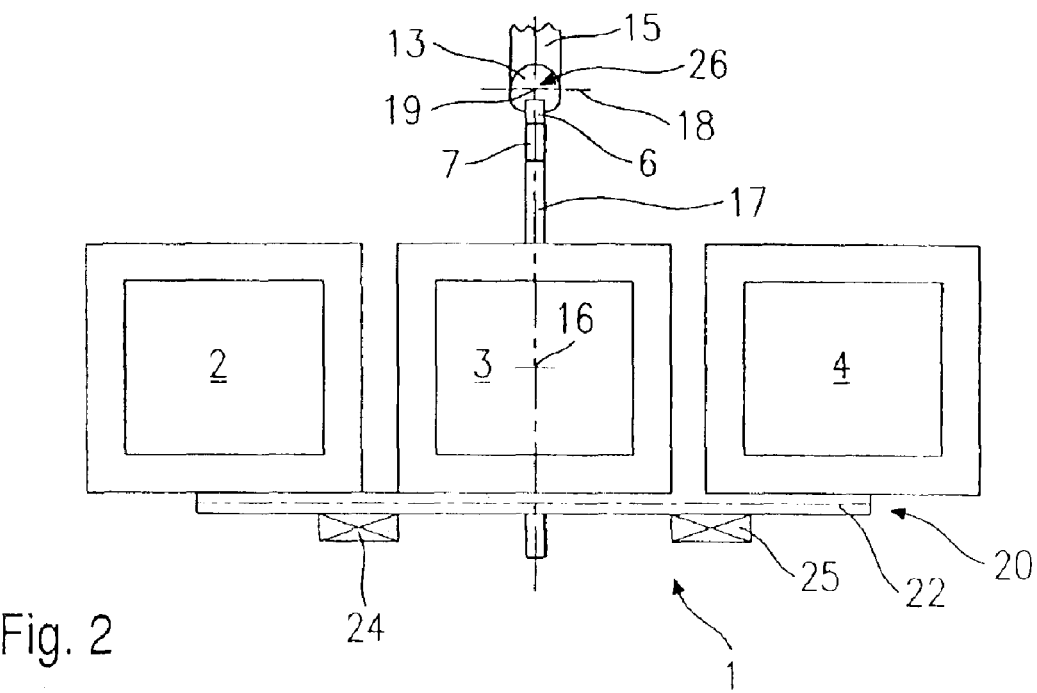
FIG. 2 shows a front view of the support according to the preferred embodiment.

FIG. 2 shows the support 1 according to the preferred embodiment to support the equipment 2, 3, 4, in a front view. Previously described components are given corresponding reference symbols in all figures, so that a repeated description is unnecessary.

In FIG. 2, the supplementary weights 24, 25, by which, with the given inclination of the support arm, the centre of gravity 16 can be moved with fine adjustment below the suspension point 26 at the intersection point of the axes 18, 19, are fixed to the support 1. In particular, the supplementary weights 24, 25 make it possible to change the inclination of the support arm 5, which is loaded with the equipment 2, 3, 4, in relation to the axis 19. This may be required, for instance, if the pieces of equipment 2, 4 are arranged at different distances from the centre of the transverse support 20, where the transverse support 20 is joined to the support arm 5, and/or if the pieces of equipment 2, 4 have different weights, or if the piece of equipment 3 (in relation to its centre of gravity) is not fixed centrally on the transverse support 20.

The supplementary weights 24, 25 are outstandingly easy to attach and remove, so that in particular it is possible to compensate at short notice for changes of centre of gravity which occur at short notice, e.g. because another small piece of equipment is placed on the piece of equipment 2.

Figure 3:
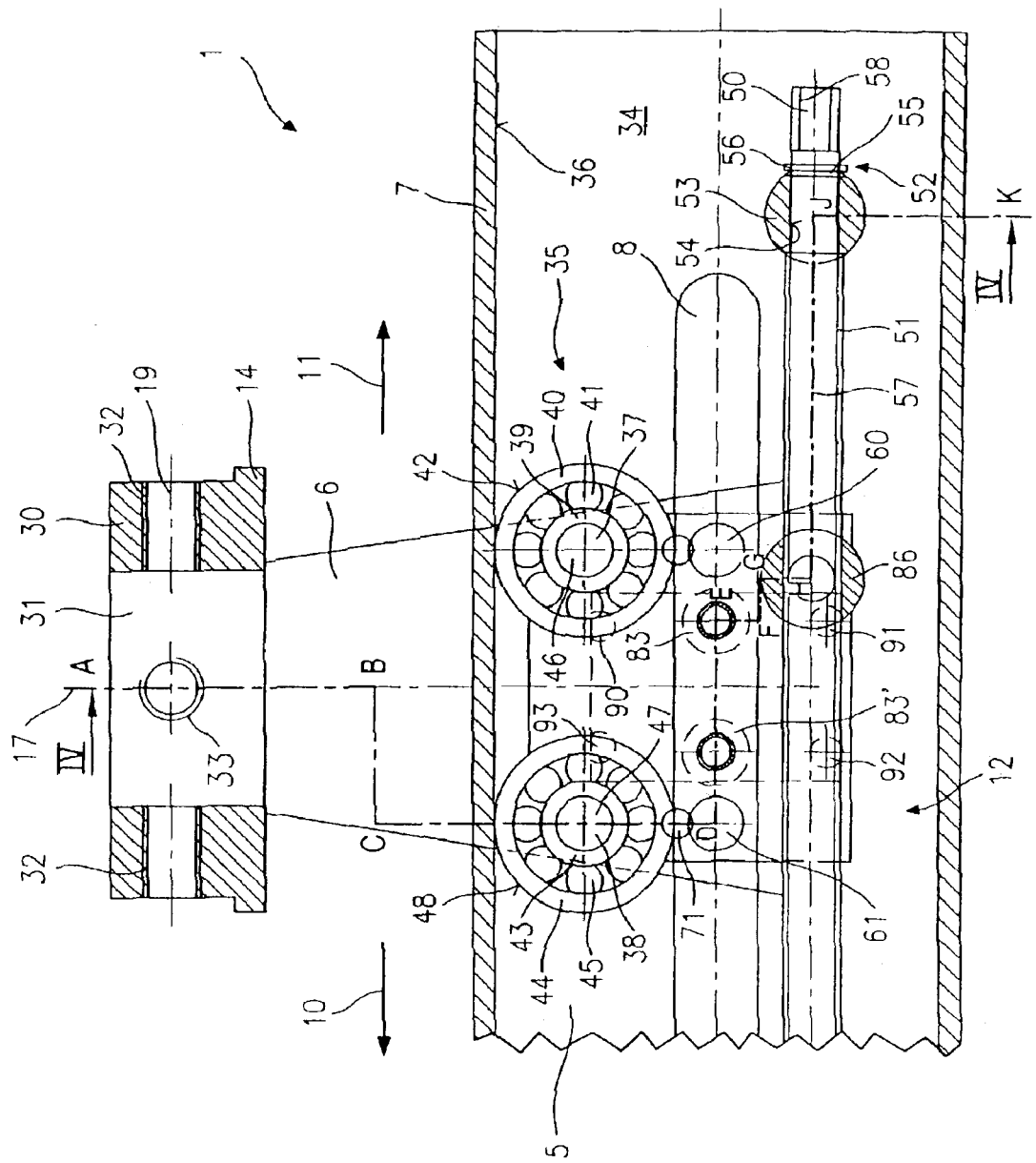
FIG. 3 shows the section of the support which is marked III in FIG. 1 in a selective cross-section.

FIG. 3 shows, in cross-section, that section of the support 1 according to the preferred embodiment which is marked III in FIG. 1.

The fixing device 6 of the support 1 has a connecting part 30 to fix the ball-and-socket joint 13 or similar. In the preferred embodiment, the connecting part 30 has the thread 32, 33, which is interrupted by the recess 31.

The fixing device 6, which engages with the inner space 34 of the connecting section 7 of the support arm 5 through the recesses 8, 9, has a locking device 35 which is arranged in the inner space 34, to lock the fixing device 6 in relation to the support arm 5. For this purpose, the support arm 5, in particular the connecting section 7 of the support arm 5, is in the form of a hollow body, which has a hollow profile, thus forming the inner space 34, particularly in the area of the connecting section 7. In the preferred embodiment, the locking device 35 is arranged in the area where the engagement point 12, at which the fixing device 6 engages with the connecting section 7 of the support arm 5, is situated. The support arm 5 has, on the connecting section 7 on the side of the inner space 34, a running surface 36, on which running wheels 37, 38 roll when the locking device 35 of the fixing device 6 is moved in relation to the support arm 5. The weight of the support arm 5, which is loaded with the equipment 2, 3, 4, is transmitted to the fixing device 6 via the running wheels 37, 38.

The running wheel 37 has an inner bearing shell 39 and an outer bearing shell 40, between which bearing balls 41 are arranged, thus forming a ball bearing. The inner bearing shell 39 of the running wheel 37 is connected to a pin 46, and on the outer bearing shell 40 a running wheel surface 42, on which the running wheel 37 rolls on the running surface 36 of the connecting section 7, is formed.

The running wheel 38 is constructed correspondingly to the running wheel 37. The running wheel 38 has an inner bearing shell 43, an outer bearing shell 44, and bearing balls 45 arranged between them, thus forming a ball bearing. The inner bearing shell 43 is connected to the pin 47, and on the outer bearing shell 44 a running wheel surface 48, which rolls on the running surface 36 of the connecting section 7 when the fixing device 6 moves in relation to the connecting section 7 of the support arm 5, is formed.

The locking device 35 is moved in relation to the support arm 5 via a spindle 50, which has a spindle thread 51 and a bearing section 52. On the bearing section 52, the spindle 50 is carried by a bearing pin 53 in the connecting section 7 of the support arm 5. For this purpose, the bearing pin 53 has a transverse hole 54, through which the threadless bearing section 52 of the spindle 50 is fed. The spindle 50 is secured in a parallel direction to the spindle axis 57 by a blocking ring 56 which is fitted in a radially surrounding groove 55. The spindle 50 also has, on its bearing section 52, an external hexagon 58, to which a suitable tool or adjustment device can be applied to activate the spindle 50. When the spindle 50 is activated, it is rotated around its spindle axis 57, so that the spindle thread 51 is rotated depending on the direction of activation. The tool or activation device can act on the spindle 50 otherwise than via the external hexagon 58. For instance, an internal hexagon on the spindle 50 in the area of the bearing section 52, or another force or positive connection, can be provided.

Figure 4:
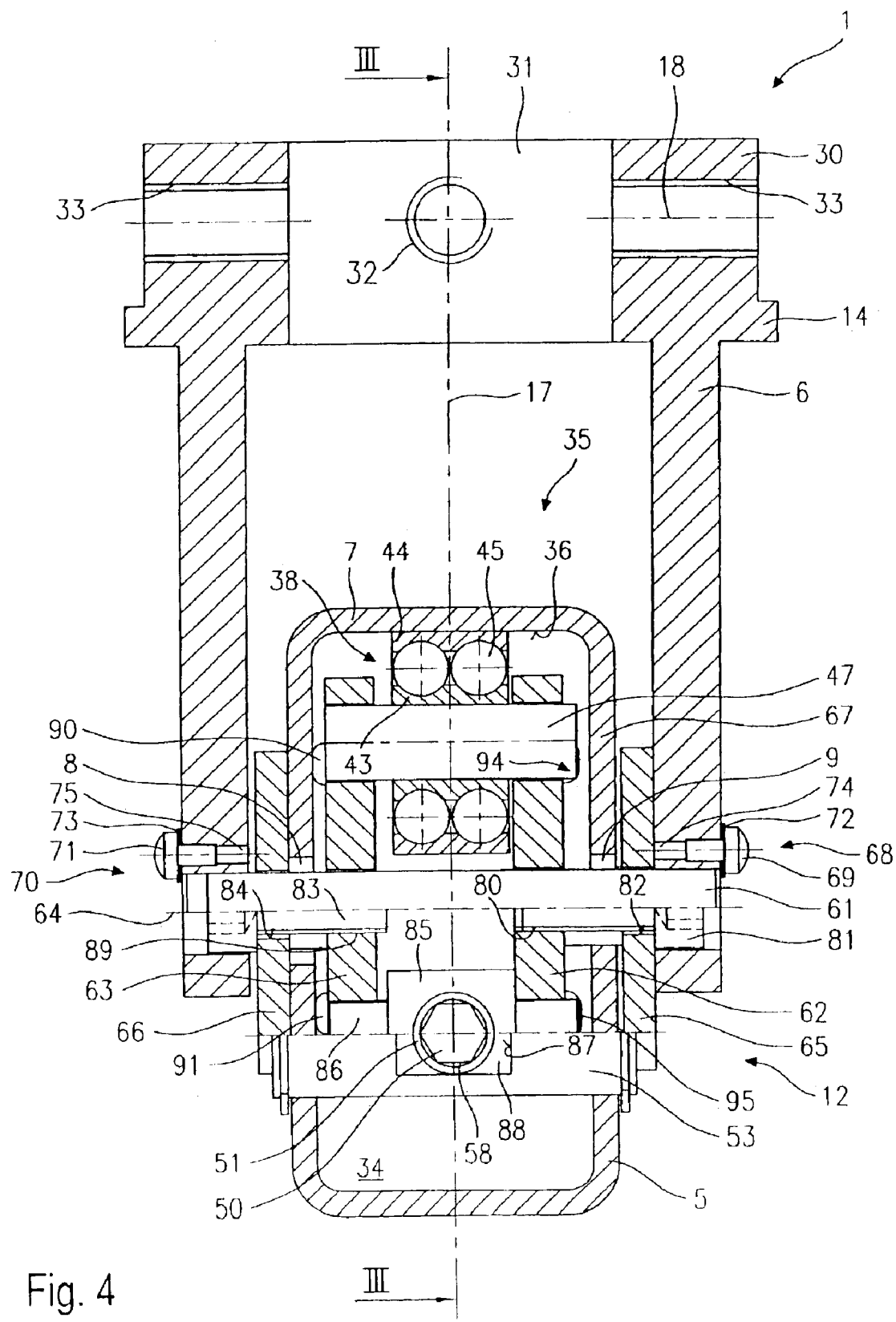
FIG. 4 shows the support according to the preferred embodiment, in a cross-section along the cross-section line along points A to K, marked IV in FIG. 3.

The support 1 of the preferred embodiment is described in more detail below, with additional reference to FIG. 4. FIG. 4 shows a cross-section along the cross-section line along points A to K, marked IV in FIG. 3. Also, FIG. 3 is a cross-section along the cross-section line marked III in FIG. 4.

The fixing device 6 has pins 60, 61, by which the first section 14 (which is outside the inner space 34) of the fixing device 6 is connected to the locking device 35. Also, locking plates 62, 63, which are guided onto the pins 60, 61 in a parallel direction to the pin axis 64 of the pin 61, are provided. The locking plates 62, 63 can therefore be moved in a parallel direction to the pin axis 64 of the pin 61. The pin 47, on which the running wheel 38 is arranged, is carried in the locking plates 62, 63. Additionally, the pin 46, on which the running wheel 37 is arranged, is carried in the locking plates 62, 63. The pins 46, 47 are guided in the locking plates 62, 63 so that they can be moved in a parallel direction to the pin axis 64 of the pin 61. The locking plates 62, 63 are arranged in the inner space 34 of the connecting section 7. The fixing device 6 also has the locking plates 65, 66, locking plate 65 being opposite to locking plate 62 in relation to the wall 67 and locking plate 66 being opposite to locking plate 63 in relation to the wall 67. The locking plates 65, 66 are carried on the pins 60, 61 so that they can be moved in a parallel direction to the pin axis 64 of the pin 61. To prevent release or movement of the pins 60, 61 in relation to the first section 14 of the fixing device 6, which is outside the inner space 34 of the connecting section 7, securing bolts 68 to 71, which for self-securing are screwed into threaded holes 74, 75 of the first section 14 of the fixing device 6 with spring elements 72, 73, are provided.

The locking device 35 has a locking bolt 81 which is screwed into a thread 80 of the locking plate 62, is partly arranged in the recess 9 of the connecting section 7, and is fed through a recess 82, which is preferably in the form of a hole. When the locking bolt 81 is tightened, it is supported on the locking plate 65, so that the two locking plates 62, 65 are moved onto each other. For locking, a locking force is transmitted onto the locking plates 62, 65 by the locking bolt 81, so that they are pressed from both sides against the wall 67 of the connecting section 7. The resulting static friction forces result in a connection, which can be released, between the fixing device 6 and the connecting section 7 of the support arm 5.

Correspondingly, a locking bolt 83 engages with a thread 89 of the locking plate 63, the locking bolt 83 being supported on the locking plate 66 when it is tightened, and being fed through a recess 84 in the locking plate 66. The locking bolt 83 is partly arranged in the recess 8 of the connecting section 7 of the support arm 5. When the locking bolt 83 is tightened with a locking force, a locking force is applied to the locking plates 63, 66, so that a connection, which can be released, and which is based on the static friction forces which occur between the locking plates 63, 66 and the wall 67 of the connecting section 7, between the locking device 35 of the fixing device 6 and the connecting section 7 of the support arm 5 is created.

When a locking force is applied to the two locking bolts 81, 83, the locking device 35 is locked in relation to the connecting section 7 of the support arm 5. By releasing the locking bolts 81, 84, the locked locking device 35 is released, so that the locking device 35 of the fixing device 6 can be moved in relation to the connecting section 7 of the support arm 5.

To move the locking device 35, the spindle 50, which is fed through a spindle guide 85 of the locking device 35, is used. The spindle guide 85 is fixed on a holding pin 86 which is oriented transversely to the spindle axis 57, the locking plates 62, 63 being guided on the holding pin 86 so that they can be moved in a parallel direction to the pin axis 64 of the pin 61. When the spindle 50 is activated, it rotates around the spindle axis 57, so that, depending on the direction of rotation, the locking device 35 and thus the whole fixing device 6 is moved relative to the connecting section 7 in the direction 10 or 11. In this way the engagement point 12, at which the fixing device 6 engages with the connecting section 7 of the support arm 5, can be continuously changed by means of the spindle 50.

In the recess 87, which is formed transversely to the longitudinal axis of the bearing pin 53, a bearing element 88, in which the transverse hole 54 is formed, is provided. The spindle 50 is guided at one end in the transverse hole 54 of the bearing pin 53 and in the spindle guide 85. More guidance, corresponding to the guidance by the bearing element 88 and spindle guide 85, can optionally be provided at the other end of the spindle 50.

In the above description, the locking of the locking device 35 by means of the locking bolts 81, 83 is described in detail. To achieve even application of the locking plates 62, 63, 65, 66, as well as the previously described locking bolts 81, 83, two further locking bolts are provided. In FIG. 3, the locking bolt 83' is arranged next to the locking bolt 83. The remaining locking bolt is arranged symmetrically to the locking bolt 83' in relation to the intersection line marked III in FIG. 4.

In the preferred embodiment, friction bodies 90 to 93 are provided on the locking plate 63, and when the locking device 35 is locked by the locking force, they are pressed against the wall 67 of the connecting section 7 of the support arm 5, to apply the required static friction force. Correspondingly, four friction bodies, of which friction bodies 94, 95 are shown in FIG. 4, are also provided on the locking plate 62. To achieve specially good friction between the friction bodies 90 to 95 and the wall 67 of the connecting section 7, it is advantageous that the materials of the friction bodies 90 to 95 are suited to the material of the wall 67 of the connecting section 7. For instance, if the wall 67 of the connecting section 7 is made of a metallic material, the friction bodies 90 to 95 can consist, for example, of a rubber mixture which is suited to it. Corresponding friction bodies can also be provided on the locking plates 65, 66 at the side of the wall 67 of the connecting section 7. A further advantage of the friction bodies 90 to 95 is that unevennesses in the surface of the locking plates 62, 63, 65, 66 and the inner and outer sides of the wall 67 of the connecting section 7 are compensated for, since the contact is not over the whole surface. In this respect, it is a further advantage if the friction bodies 90 to 95 are made of an elastic material.

An unevenness in the surface of the wall 67 of the connecting section 7 can be given, in particular, by a weld seam by which the support arm 5 is welded.

If the fixing unit 6 is moved in the directions 10, 11, and the C-bow-shaped support arm 5 is positioned horizontally, both running surfaces 42, 48 of the running wheels 37, 38 lie simultaneously on the running surface 36 of the connecting section 7. In particular, it is thus possible to establish whether the centre of gravity 16 of the loaded support arm 5, for a given inclination of the support arm 5, is at least approximately below the suspension point 26, on which the support is suspended by means of the fixing device 6. Outside the horizontal position, a torque occurs around a bearing axis of the running wheel 37 or 38, until one of the pins 60 or 61 is in the recesses 8, 9.

The invention is not restricted to the described embodiment. In particular, the support arm 5 can be in a different form, e.g. T-shaped, or consist of several parts.

What is claimed is:

1. A support for supporting at least one piece of equipment, comprising a visual display unit (VDU), said support including a support arm on which the equipment is at least indirectly fixable, a fixing device which engages with a connecting section of the support arm for suspending the connecting section of the support arm for suspending the support and having a changeable engagement point for shifting the center of gravity of the loaded support arm for a given inclination of the support arm so that said support arm lies at least approximately below a suspension point on which the support is suspended by said fixing device, said fixing device comprising a ball and socket joint for a torque less suspension of the support relative to a horizontal axis, at least the connecting section of the support arm having a hollow profile so as to form an internal space at least in the area of the connecting section, said connecting section having at least two recesses arranged opposite each other, and through which the fixing device engages with the internal space of the connecting section of the support arm, and wherein a locking device for the fixing device for locking the fixing device relating to the support arm is arranged at least substantially within the internal space of the connecting section of the support arm.

2. A support for supporting at least one piece of equipment, comprising a visual display unit (VDU), said support including a support arm on which the equipment is at least indirectly fixable; a fixing device which engages with a connecting section of the support arm for suspending the support and having a changeable engagement point for shifting the center of gravity of the loaded support arm for a given inclination of the support arm so that said support arm lies at least approximately below a suspension point on which the support is suspended by means of the fixing device, said fixing device comprising a ball and socket joint for a torque less suspension of the support relative to at least one axis, at least the connecting section of the support arm comprising an internal space, which is formed at least in the area of the connecting section, said fixing device engaging with the internal space of the connecting section for the support arm; and wherein a locking device for the fixing device for locking the fixing device relative to the support arm is arranged at least substantially in the internal space of the connecting section of the support arm.

3. A support according to claim 2, wherein the internal space of the connecting section of the support arm is formed by a hollow profile of at least the connecting section of the support arm.

4. A support according to claim 3, wherein the connecting section has at least two recesses arranged opposite each other, and through recesses, which the fixing device engages to the inner space of the connecting section of the support arm.

5. A support according to claim 1 or 2, wherein the support arm is bow-shaped.

6. A support according to claim 1 or 2, wherein the locking device has at least one locking plate to which a locking force is applicable for locking a side of the internal space of the connecting section against a wall of the connecting section.

7. A support according to claim 6, wherein a further locking plate, which is arranged at least substantially opposite to the first said locking plate relative to the wall of the connecting section is associated with the locking plate to facilitate applying the locking force to both locking plates against each other, so as to thereby lock the fixing device relative to the support arm.

8. A support arm according to claim 7, wherein the locking device includes a locking bolt, which engages with a screwthread on said first locking plate and is supported at least indirectly on said further locking plate upon being tightened.

9. A support according to claim 8, wherein the engagement point at which the fixing device engages with the connecting section of the support arm is continuously changeable.

10. A support according to claim 1 or 2, wherein the engagement point is changed by operation of a spindle, which is carried in the support arm, and along which spindle the fixing device, is movable.

11. A support according to claim 1 or 2, wherein supplementary weights are attachable to the support arm, for shifting the center of gravity of the loaded support arm for a given inclination of the support arm at a fine adjustment below the suspension point.

* * * * *